(12) United States Patent
Pick et al.

(10) Patent No.: US 9,913,650 B2
(45) Date of Patent: Mar. 13, 2018

(54) ANCHOR FOR SHAPE MEMORY ALLOY WIRE AND ACTUATOR

(71) Applicant: Dean Pick, Vancouver (CA)

(72) Inventors: Dean Pick, Vancouver (CA); Dayn Longlade, Vancouver (CA)

(73) Assignee: Dean Pick, Vancouver BC (CA)

( * ) Notice: Subject to any disclaimer, the term of this patent is extended or adjusted under 35 U.S.C. 154(b) by 348 days.

(21) Appl. No.: 14/964,174

(22) Filed: Dec. 9, 2015

(65) Prior Publication Data
US 2017/0164948 A1 Jun. 15, 2017

(51) Int. Cl.
| | |
|---|---|
| *A61B 17/04* | (2006.01) |
| *A61B 17/12* | (2006.01) |
| *A61B 17/068* | (2006.01) |
| *A61B 17/00* | (2006.01) |
| *A61B 17/06* | (2006.01) |

(52) U.S. Cl.
CPC .......... *A61B 17/12* (2013.01); *A61B 17/0401* (2013.01); *A61B 17/0487* (2013.01); *A61B 17/0682* (2013.01); *A61B 17/12009* (2013.01); *A61B 17/0466* (2013.01); *A61B 17/06166* (2013.01); *A61B 2017/00867* (2013.01); *A61B 2017/00871* (2013.01); *A61B 2017/0414* (2013.01); *A61B 2017/0454* (2013.01); *A61B 2017/0464* (2013.01)

(58) Field of Classification Search
CPC . A61B 17/04; A61B 17/0401; A61B 17/0487; A61B 17/0682; A61B 17/12; A61B 17/12009; A61B 17/122; A61B 2017/00867; A61B 2017/0414; A61B 2017/0446; A61B 2017/0454; A61B 2017/0456; A61B 2017/0459; A61B 2017/0461; A61B 2017/0462; A61B 2017/0464; A61B 2017/0496; A61B 2017/12004; A61L 17/00; Y10T 24/3933
See application file for complete search history.

(56) References Cited

U.S. PATENT DOCUMENTS

| | | | |
|---|---|---|---|
| 3,058,185 A | * | 10/1962 | Clayton .................. F16G 11/06 24/135 R |
| 4,945,727 A | | 8/1990 | Whitehead et al. |
| 5,176,544 A | | 1/1993 | AbuJudom, II et al. |

(Continued)

*Primary Examiner* — Ryan J Severson
(74) *Attorney, Agent, or Firm* — Kagan Binder, PLLC

(57) ABSTRACT

The present invention is an anchor for a thermally responsive ligature that deforms when heated. The ligature has an engaging segment for engaging the anchor with two clamping portions and a curved portion. The anchor is made from a thermally and/or electrically conductive material and has an engaging surface for engaging a curved portion of the ligature. The clamping portions of the engaging segment of the ligature pass between the body and the clamping component when the curved portion of the engaging segment is engaging the engaging surface of the anchor body. Then, portions of the clamping component can be moved towards the anchor body to reconfigure the clamping component so that the portions of the clamping component press the clamping portions of the engaging segment of the ligature against the anchor body and maintain the engaging segment of the ligature in thermal or electrical communication with the anchor body.

20 Claims, 5 Drawing Sheets

(56) References Cited

U.S. PATENT DOCUMENTS

| | | | | |
|---|---|---|---|---|
| 5,330,442 | A * | 7/1994 | Green | A61B 17/0487 606/151 |
| 5,376,101 | A * | 12/1994 | Green | A61B 17/0487 606/151 |
| 5,441,509 | A * | 8/1995 | Vidal | A61B 17/122 24/115 A |
| 6,015,417 | A * | 1/2000 | Reynolds, Jr. | A61B 17/064 606/151 |
| 6,247,678 | B1 | 6/2001 | Hines et al. | |
| 6,374,608 | B1 | 4/2002 | Corris et al. | |
| 6,468,293 | B2 * | 10/2002 | Bonutti | A61B 17/0487 606/148 |
| 6,475,230 | B1 * | 11/2002 | Bonutti | A61B 17/0487 606/232 |
| 6,511,498 | B1 * | 1/2003 | Fumex | A61B 17/0401 606/232 |
| 6,524,325 | B2 * | 2/2003 | Shaw | A61B 17/0483 606/207 |
| 6,574,958 | B1 | 6/2003 | MacGregor | |
| 6,818,009 | B2 * | 11/2004 | Hart | A61B 17/0469 606/151 |
| 7,326,233 | B2 * | 2/2008 | Hart | A61B 17/0469 606/151 |
| 7,367,534 | B2 * | 5/2008 | Franks, Jr. | F16L 3/10 174/40 CC |
| 7,650,914 | B2 * | 1/2010 | Bogursky | H01R 4/188 140/105 |
| 7,867,254 | B2 * | 1/2011 | Hart | A61B 17/0469 606/151 |
| 7,926,520 | B2 * | 4/2011 | Bogursky | H01R 4/188 140/105 |
| 8,113,243 | B2 * | 2/2012 | Bogursky | H01R 4/188 140/105 |
| 8,350,959 | B2 | 1/2013 | Topliss et al. | |
| 8,397,485 | B2 | 3/2013 | Wood et al. | |
| 8,679,154 | B2 * | 3/2014 | Smith | A61B 17/064 606/219 |
| 8,679,156 | B2 * | 3/2014 | Smith | A61B 17/064 606/219 |
| 8,695,334 | B2 | 4/2014 | Lewis et al. | |
| 8,701,406 | B2 * | 4/2014 | Lewis | E21B 33/064 60/527 |
| 8,753,373 | B2 * | 6/2014 | Chau | A61B 17/0487 606/144 |
| 8,939,180 | B2 * | 1/2015 | Bogursky | H01R 4/188 140/105 |
| 9,022,682 | B2 | 5/2015 | Skurkis et al. | |
| 9,055,939 | B2 * | 6/2015 | Fujisaki | A61B 17/0487 |
| 9,084,596 | B2 * | 7/2015 | Stanley | A61B 17/0401 |
| 9,145,903 | B2 * | 9/2015 | Lewis | E21B 33/064 |
| 9,414,833 | B2 * | 8/2016 | Stone | A61B 17/0401 |
| 9,421,008 | B2 * | 8/2016 | Burkhart | A61B 17/0401 |
| 9,474,525 | B2 * | 10/2016 | Smith | A61B 17/064 |
| 9,492,158 | B2 * | 11/2016 | Stone | A61B 17/0401 |
| 9,498,202 | B2 * | 11/2016 | Jafari | A61B 17/0401 |
| 9,700,306 | B2 * | 7/2017 | Smith | A61B 17/064 |
| 2001/0021862 | A1 * | 9/2001 | Bonutti | A61B 17/0487 606/232 |
| 2001/0039433 | A1 * | 11/2001 | Shaw | A61B 17/0483 606/207 |
| 2002/0065536 | A1 * | 5/2002 | Hart | A61B 17/0469 606/232 |
| 2004/0236372 | A1 * | 11/2004 | Anspach, III | A61B 17/0487 606/232 |
| 2004/0261411 | A1 * | 12/2004 | MacGregor | F03G 7/065 60/527 |
| 2005/0038459 | A1 * | 2/2005 | Hart | A61B 17/0469 606/157 |
| 2008/0091236 | A1 * | 4/2008 | Hart | A61B 17/0469 606/232 |
| 2008/0281356 | A1 * | 11/2008 | Chau | A61B 17/0487 606/232 |
| 2012/0017583 | A1 * | 1/2012 | Lewis | E21B 33/064 60/529 |
| 2012/0165865 | A1 * | 6/2012 | Fujisaki | A61B 17/0487 606/232 |
| 2013/0138123 | A1 * | 5/2013 | Stone | A61B 17/0401 606/148 |
| 2013/0158601 | A1 * | 6/2013 | Stone | A61B 17/0401 606/232 |
| 2013/0226237 | A1 * | 8/2013 | Stanley | A61B 17/0401 606/232 |
| 2014/0031864 | A1 * | 1/2014 | Jafari | A61B 17/0401 606/232 |
| 2014/0121681 | A1 * | 5/2014 | Fujii | A61B 17/0401 606/144 |
| 2016/0270776 | A1 * | 9/2016 | Miraki | A61B 17/0487 |
| 2017/0164948 | A1 * | 6/2017 | Pick | A61B 17/0682 |
| 2017/0224329 | A1 * | 8/2017 | Ono | A61B 17/0487 |

* cited by examiner

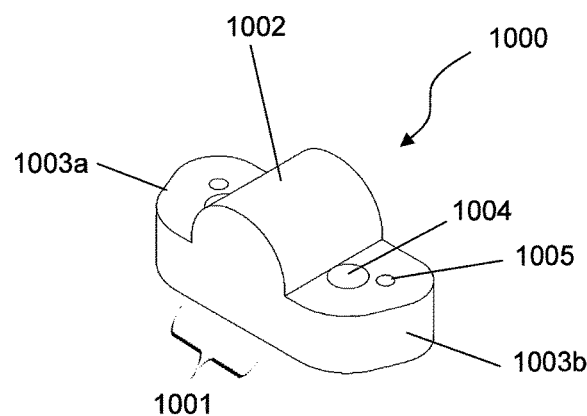
Fig. 10
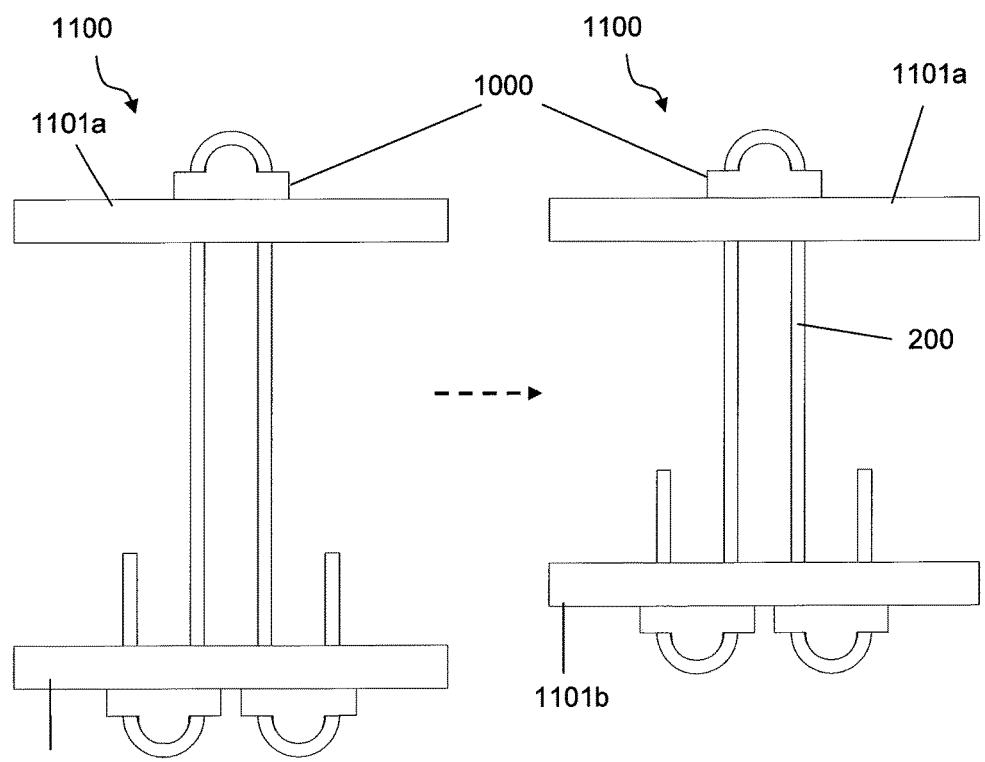
Fig. 11a
Fig. 11b

ND ACTUATOR

ANCHOR FOR SHAPE MEMORY ALLOY WIRE AND ACTUATOR

FIELD OF THE INVENTION

The present invention relates to mechanisms to attach thermally responsive ligature to members of a device where the thermally responsive ligature exerts force on the members to move them relative to each other, and to actuators employing such mechanisms.

BACKGROUND OF THE INVENTION

Active material elements such as shape memory alloy (SMA) wires are used in various devices, such as actuators and smart devices to cause displacements of structural members of the devices by activation of the active elements. This may be done, for example, by passing current through SMA wire, thereby causing it to heat, resulting in contraction of the wire and the application of force to the members it is attached to.

However, when an SMA wire is heated, normally all portions of the wire contract, or attempt to contract, including those portions that are directly attached to a structural member. Such repeated deformation or contraction in the portion(s) of the wire attached to members can result in failure of the device. One failure mode is failure by fatigue due to uneven stress distribution when contraction occurs along a curve. Another failure mode is slide-through of wire at the attachment point leading to pull-out.

SUMMARY OF THE INVENTION

The present invention provides an anchor for a thermally responsive ligature that deforms when heated. The ligature is configured to have an engaging segment for engaging the anchor, which is a segment of the ligature with two clamping portions and a curved portion between the clamping portions. The anchor includes a body and a configurable clamping component. The anchor body is made, at least in part, from a thermally and/or electrically conductive material and has an engaging surface for engaging the curved portion of the engaging segment of the ligature. The clamping component is configured to allow the clamping portions of the engaging segment of the ligature to pass between the body and the clamping component when the curved portion of the engaging segment is engaging the engaging surface of the anchor body. Then, portions of the clamping component proximate to the clamping portions of the engaging segment of the ligature can be moved towards the anchor body to reconfigure the clamping component so that the portions of the clamping component press the clamping portions of the engaging segment of the ligature against the anchor body and maintain the engaging segment of the ligature in thermal or electrical communication with the anchor body.

The anchor body may be attachable to a first member of a device having a second member connected to the first member by a thermally responsive ligature. When the anchor body is attached to the first member of the device, the engaging segment of the ligature is then in thermal and/or electrical communication with the anchor body, with the curved portion of the engaging segment of the ligature engaging the engaging surface of the anchor body, and the clamping portions of the ligature pressed against the anchor body by the clamping component after the clamping component has been reconfigured to maintain the engaging segment of the ligature in thermal and/or electrical communication with the anchor body. Then, when the ligature is heated, the ligature deforms and applies force to the anchor body towards the second member, causing the members to move towards each other. When the ligature is heated, the temperature increase in the engaging segment of the ligature is sufficiently limited by heat transfer to the anchor body and/or by reduction of current passing through the engaging segment of the ligature because of current passing through the anchor body that deformation of the engaging segment is prevented or substantially reduced relative to segments of the ligature not in contact with the anchor.

In some embodiments, the curved portion of the engaging segment of the ligature may have two curved sub-portions and a flattened sub-portion between those two curved sub-portions. In such embodiments, the engaging surface of the anchor body has a flat portion for engaging a portion of the flattened sub-portion of the engaging segment of the ligature.

In some preferred embodiments, the engaging surface of the anchor body and the curved portion of the engaging segment are continuously curved so that when the clamping portions of the engaging segment of the ligature are clamped against the anchor body, the ligature engages the curved surface of the anchor body along the full length of the engaging segment of the ligature.

The curved portion of the of the engaging segment of the ligature may have a 180 degree curve so that when the clamping portions of the ligature are pressed against opposing sides of the anchor body, the clamping portions of the ligature are substantially parallel to each other.

The ligature is preferably electrically conductive and a portion of the anchor body that includes the engaging surface is preferably electrically conductive so that when the engaging segment of the ligature is engaged with the anchor body, the electrically conductive portion of the anchor body electrically connects the clamping portions of the engaging segment of the ligature. The electrically conductive portion of the anchor body preferably presents an electrical resistance less that the electrical resistance of the engaging segment of the ligature, so that when a current, I, flows through segments of the ligature not in contact with the anchor, the amount of current flowing through the engaging segment of the ligature is less than one-half of I, or more preferably substantially less than I. The anchor body may be attachable to a first member of a device having a second member attached to the first member by a thermally responsive ligature. In this device, the engaging segment of the ligature may be electrically engaged with the anchor body, with the curved portion of the engaging segment of the ligature engaging the engaging surface of the anchor body, and the clamping portions of the ligature being pressed against the anchor body by the clamping component after the clamping component has been reconfigured to maintain the engaging segment of the ligature in electrical communication with the anchor body. Then, when sufficient current passes though the ligature to cause the ligature to heat sufficiently to cause some portions of the ligature to deform, the ligature applies force to the anchor body towards the second member, causing the members to move towards each other. Deformation of the engaging segment of the ligature is substantially prevented by the fraction of the current flowing through the engaging segment of the ligature being limited as a result of the current flowing through the anchor body. The anchor body is preferably made of metal, such as brass. The anchor may also include a feature for electrically connecting the electrically conductive portion of the anchor body to a power source. The feature for electrically connecting the electrically conductive portion of the anchor body to a power source may be a solder pad and the power source is then connectable to the feature through a mating solder pad on a printed circuit board.

The ligature is preferably a shape memory alloy wire. Alternatively, the ligature may be a shape memory alloy tape.

The anchor body and clamping component may be integrally formed from a single piece of metal. The anchor body may be a U-shaped portion of the piece of metal, and the clamping component may consist of two arms, each arm being bendably connected to one end of the anchor body and extending along a portion of a side of the anchor body proximate to and spaced apart from the anchor body. In such embodiments, the anchor includes two openings sized to accommodate the ligature, each opening being proximate to the anchor body and to one of the arms. In such embodiments, the clamping component is reconfigurable by applying force to each of the two arms towards the anchor body so that the force causes the arms to bend so that when the curved portion of the engaging segment is engaging the engaging surface of the anchor body and the clamping portions of the engaging segment of the ligature are between the anchor body and the arms, each arm is then pressed against one of the clamping portions of the engaging segment of the ligature, maintaining the engaging segment of the ligature in thermal and electrical communication with the anchor body.

The clamping component may be a metal ring having an inner diameter greater than the sum of (a) two times the thickness of the ligature and (b) the thickness of the portion of the anchor body proximate to the clamping portions of the engaging segment of the ligature.

The anchor may include locating features configured to receive the engaging segment of the ligature. The locating features may include two grooves as locating features, each groove being configured to receive one the clamping portions of the engaging segment of the ligature.

The invention also provides an actuator having first and second members, a thermally responsive ligature connected to the second member, and an embodiment of an anchor as described above attached to the first member. The engaging segment of the ligature is thermally and/or electrically engaged with the anchor body with the curved portion of the engaging segment of the ligature engaging the engaging surface of the anchor body, and the clamping portions of the ligature pressed against the anchor body by the clamping component after the clamping component has been reconfigured to maintain the engaging segment of the ligature in thermal or electrical communication with the anchor body. When the ligature is heated, the ligature deforms and applies force to the engaging surface of the anchor body towards the second member, causing the members to move towards each other.

The actuator also preferably includes a biasing mechanism configured to move the first and second members back to their starting positions after the heating has been discontinued and the ligature ceases to be deformed.

The invention also provides an anchoring device that includes multiple anchors, each anchor being an anchor as described above. The anchoring device is configured so that for each of the anchors, the engaging surface of the anchor is engageable with an engaging segment of a thermally responsive ligature so that the clamping portions of the ligature are pressed against the anchor body by the clamping component of the anchor after the clamping component has been reconfigured to maintain the engaging segment of the ligature in thermal or electrical communication with the anchor body.

BRIEF DESCRIPTION OF THE DRAWINGS

FIG. 1b is annotated to identify various portions of the anchor.

FIG. 2b is annotated to identify various portions of the anchor.

FIG. 10 is a perspective view of a third embodiment of an anchor.

FIGS. 11a and 11b are side views of a simple actuator employing the third embodiment of an anchor, where an SMA wire has deformed in FIG. 11b to cause two members of the actuator to move towards each other.

DETAILED DESCRIPTION OF THE INVENTION

Figure 1A:
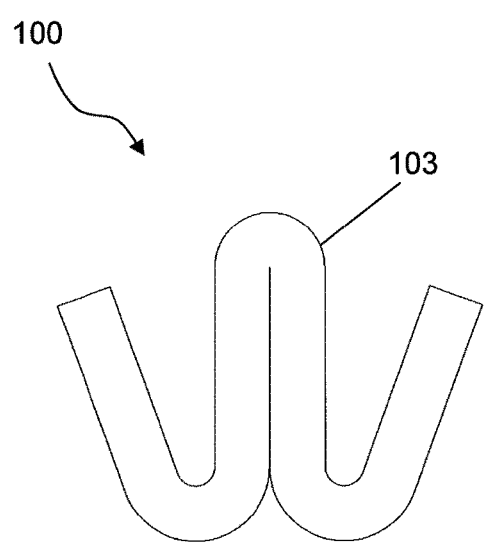
FIGS. 1a and 1b are side views of a first embodiment of an anchor.
Figure 1B:
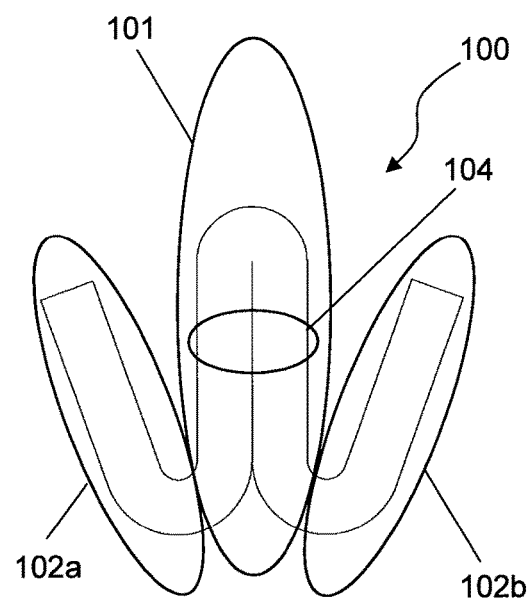

A first embodiment of an anchor 100 is shown in FIG. 1, and also in FIGS. 3-6. FIG. 1a is a side view of the generally "W" shaped anchor which is preferably formed from a single piece of metal, such as brass. The anchor 100 has two main components, which are indicated in FIG. 1b, being an anchor body 101 and a clamping component. In this embodiment, the clamping component consists of two separate arms 102a and 102b, each arm being connected to one end of the anchor body 101. The material used to form the anchor is selected so that the arms 102a, 102b are bendably attached to the body 101 so that force can be applied to the outer sides of the arms 102a, 102b towards the body, causing the arms 102a, 102b to move towards to the body 101 and remain in the bent or deformed state after the force is removed. The anchor body 101 has an engaging surface 103 that is configured for engagement with an engaging segment of a thermally responsive ligature, such as SMA wire or tape.

Shape-memory alloy (SMA, also referred to as smart metal, memory metal, memory alloy, muscle wire, and smart alloy) is an alloy that "remembers" its original shape and that when deformed returns to its pre-deformed shape when heated. The two main types of shape-memory alloys are copper-aluminium-nickel, and nickel-titanium (NiTi) alloys but SMAs can also be created by alloying zinc, copper, gold and iron. Under heating, an SMA wire in the martensite state will start to deform at a first threshold temperature ($A_s$) and change to the austenite state by the time it reaches a second (higher) temperature ($A_f$). (The austenite state may be referred to as a deformed state herein.) In the present context, the wire in the austenite state is contracted so that it is shorter in the austenite state than when in the martensite state. The wire will remain in the austenite state until the wire is cooled below a certain threshold temperature ($M_s$), which is less than $A_f$, when it will start to return to the martensite state, and will return back to the martensite state by the time the wire reaches another particular temperature ($M_f$), which is generally less than $A_s$.

The anchor body 101 is preferably made from a thermally and electrically conductive material, such as brass or other metal. It is sufficient though that a portion of the anchor body 101 including a portion of the engaging surface 103 be thermally or electrically conductive. The conductive portion of the anchor body includes one sub-portion of the body on either side of the engaging surface 103 that are thermally and electrically connected together.

For example, although it is not preferred, the anchor body may be formed from a non-conductive material with an electrically conductive coating. As another non-preferred example, the anchor body may comprise conductive material only in a central portion, such as the portion identified roughly as item 104 shown in FIG. 1b, which will electrically connect (or "short") the clamping portions 203a, 203b of the wire 200, while the remainder of the anchor 100 may be made from non-conductive material(s).

It is preferable that the entire anchor 100 be formed from a single piece of metal, such as brass, so that the anchor body 101 and clamping component are integrally formed from a single piece of metal that is both thermally and electrically conductive. The anchor may be made by machining, stamping, cutting, forming, moulding or any combination of these approaches.

The anchor body 101 of the first embodiment of an anchor may be referred to as being generally "U"-shaped, however it is generally preferred in such embodiments that two sides of the "U" are adjacent, having been pressed together as shown in FIG. 1a so that the entire anchor body 101, or at least a portion of the anchor body, such as sub-portion 104 in FIG. 1b, be thermally and preferably also electrically connected. Of course, in some embodiments, the anchor body 101 may be formed as a single unit rather than from two sides of a U-shaped piece that have been pressed together.

Figure 2A:
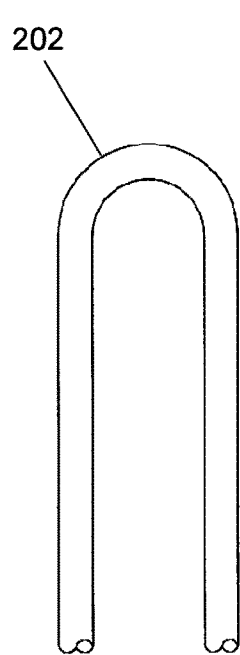
FIGS. 2a and 2b are side views of a portion of an SMA wire including an engaging segment.
Figure 2B:
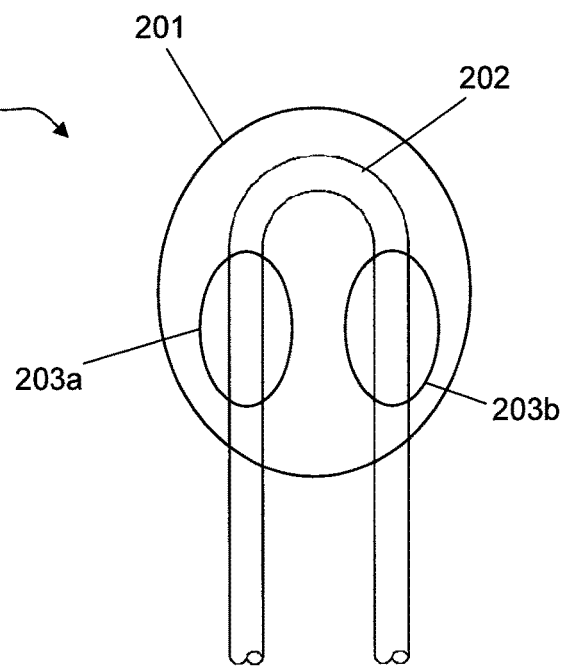

FIG. 2a shows a side view of a portion of a thermally responsive ligature, which is an SMA wire 200 having a curved portion 202 being a smooth 180 degree curve. A portion of the wire 200 is designated as the engaging segment 201, as depicted in FIG. 2b. The engaging segment 201 includes the curved portion 202 as well as two clamping portions 203a, 203b which are parallel to each other.

Figures 5, 6:
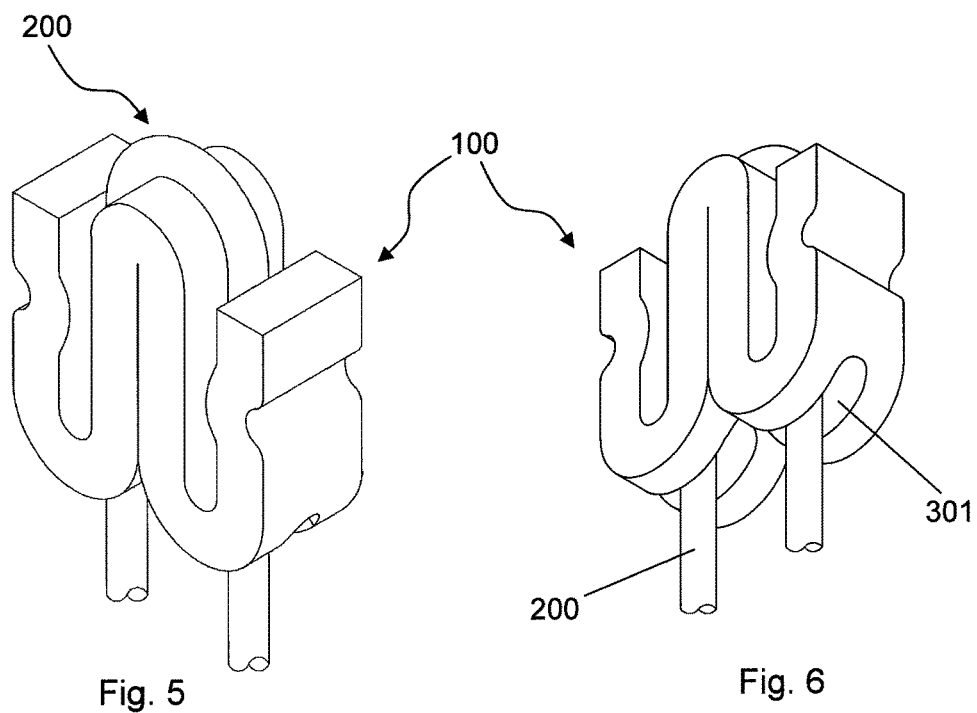
FIGS. 5 and 6 are perspective views of the first embodiment of an anchor fully engaged with the engaging segment of an SMA wire after the clamping component of the anchor has been reconfigured to maintain the engaging segment of the wire in thermal and electrical communication with the anchor body.

The anchor 100 has two openings sized and shaped to accommodate the ligature, which in the depicted embodiment are slots 301, which are best seen in FIG. 6. While in the case of SMA wire the openings could be circular with a diameter somewhat larger than the diameter of the wire, it has been found to be preferable to use slots because circular holes are more subject to deformation when the anchor is being formed from a flat strip of material which is subsequently bent into the W-shape shown in FIG. 1a. The slots can be cut or punched out of the strip of material before it is bent into the depicted W-shape.

Figures 3, 4:
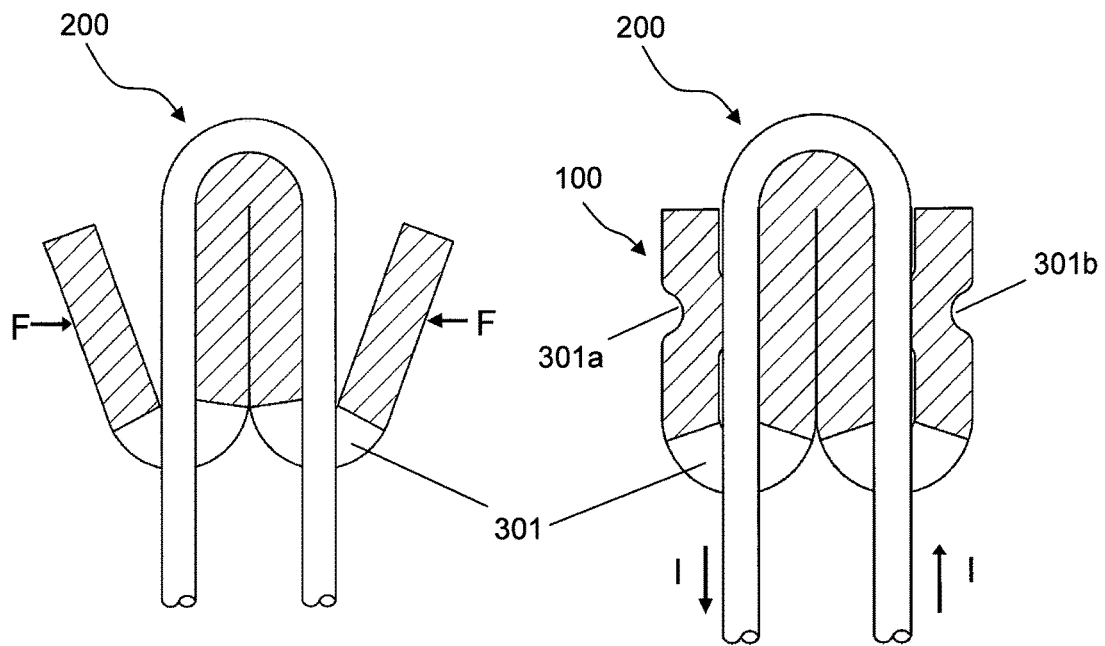
FIG. 3 is a side view of the first embodiment of an anchor engaged with the engaging segment of an SMA wire before the clamping component of the anchor has been reconfigured to maintain the engaging segment of the an SMA wire in thermal and electrical communication with the anchor body.
FIG. 4 is a side view of the first embodiment of an anchor fully engaged with the engaging segment of an SMA wire after the clamping component of the anchor has been reconfigured to maintain the engaging segment of the wire in thermal and electrical communication with the anchor body.

In order to attach the wire 200 to the anchor 100, the wire 200 is placed as depicted in FIG. 3 with the engaging segment 201 of the wire 200 engaging (i.e. in contact with) the engaging surface 103 of the anchor body 101. Placement of the wire 200 can be performed by weaving it through one slot 301, forming it over the anchor body 101 and passing it through the opposite slot 301. Alternatively the wire 200 can be loosely woven through the anchor 100 and an external tool can be used to form the curved portion 202 at which point the anchor 100 can be slid into position. In the embodiment of FIGS. 1 and 3-6, the surface 103 of the anchor body 101 has a curved portion with curvature matching the curvature of the curved portion 202 of the wire 200, and two straight parallel portions so that the wire 200 and the anchor body can be brought into contact as shown in FIG. 3 so that the engaging segment 201 of the wire 200 is in contact with the surface of the anchor body 101 along the full length of the with the wire 200 passing through the two slots 301 in the anchor 100.

Figure 12:
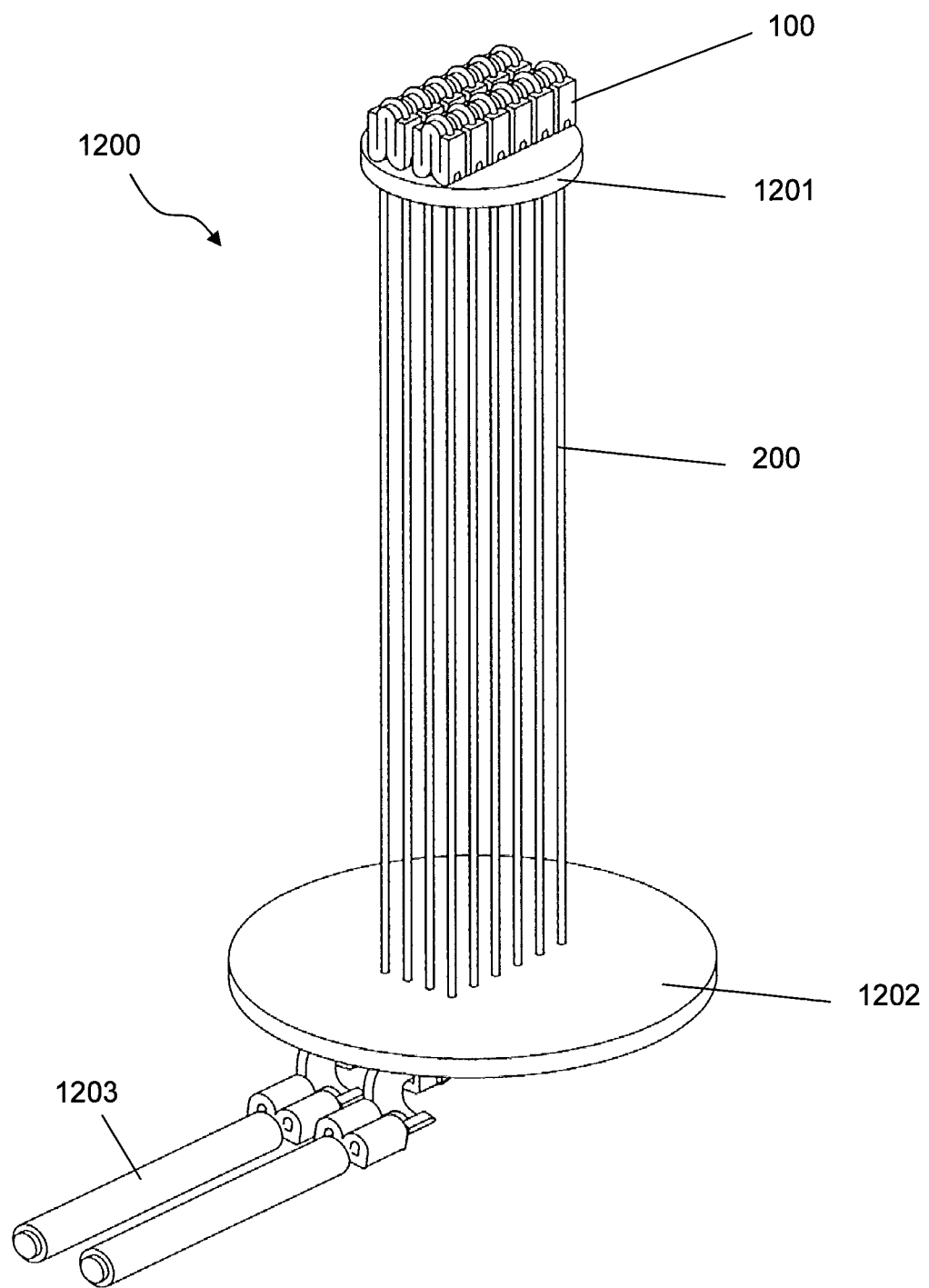
FIG. 12 is a perspective view of an actuator depicting 12 anchors in accordance with the first embodiment of an anchor attached to the upper member of the actuator.

The use of such a curved surface allows the anchor to accommodate ligature with a relatively small bending radius, this allowing for a high-density actuator design, for example, with many strands of SMA wire (see, e.g., FIG. 12).

It should be noted that, while it is preferred, it is not essential that all portions of the engaging segment of the wire be in direct engagement with the anchor body when the anchor is in use in a device. For example, where an upper portion of the engaging surface of the anchor body is flat, as in the embodiments shown in FIG. 7, the wire may not contact part of the flat portion of the anchor body. However, when in use in a device, such as an actuator, it is essential that the clamping portions of the wire be firmly clamped to the anchor body so that those clamping portions are electrically and/or thermally connected to each other via the anchor body and so that the wire can apply force to the anchor that is in turn exerted on a member of the device to which the anchor is attached.

Once the wire 200 is engaged with the anchor 100 as shown in FIG. 3, then force (such as the force marked as "F" in FIG. 3) can be applied to the outer portion of the two arms 102a, 102b towards the anchor body 101, bending the arms 102a, 102b relative to the anchor body 101 to cause the arms 102a, 102b to be brought into contact with the clamping portions 203a, 203b of the wire 200 and press the clamping portions 203a, 203b of the wire 200 against the sides of the anchor body 101, thereby maintaining the engaging segment 201 of the wire 200 in thermal and electrical communication with the anchor body 101, as shown in FIGS. 4-6. When the force is applied to only a limited vertical extent of the arms, which is generally most convenient, it may result in indentations 301a, 301b in outer portions of the arms 102a, 102b, and corresponding bulges in the inner portions of the arms 102a, 102b that press against the clamping portions 203a, 203b of the wire 200. When the clamping component is made of a relatively soft material, such as brass, the application of force may cause the brass to flow around the wire to some degree where the material forming the clamping component is softer than the SMA wire.

In addition to pressing the wire into thermal conduction with the anchor body 101, the application of such a crimping force helps ensure that any surface oxide on the wire is broken to permit good electrical communication between the wire and the anchor body 101.

In preferred embodiments, the material used to form the anchor body 101 is selected so that it provides less electrical resistance than the wire so that if a current, I, is flowing through the portions of the wire 200 outside of the engaging segment 201, which are not in contact with the anchor, then most of the current will flow through the anchor body 101 so that the current flowing through the engaging segment 201 of the wire 200 is substantially reduced. This is important because SMA wire is often activated by passing a current through it, which causes Joule heating, which in turn activates the wire 200 to transform it from martensite to austenite as discussed above (whereby it deforms by contracting and shortening). Such contraction of the wire 200 is generally useful in an actuator, for example, in order to cause a force to be created on the anchor 100 (and therefore to whatever member the anchor is attached to) relative to another member (not shown in FIGS. 3-6) connected to the wire 200 away from the anchor 100, which can be designed to cause the anchor and the member it is connected to and a second member to which the wire 200 is connected to move towards each other.

While the contraction in the segments of the wire 200 between the anchor and the other member is therefore useful and desirable, contraction in the engaging segment 201 of the wire 200 is not desirable. Even if the engaging segment 201 of the wire 200 is fixed, such as by the clamping engagement shown in FIG. 4, it is desirable to avoid the wire in the engaging segment 201 from reaching the $A_s$ threshold temperature that would cause it to start to attempt to contract because such forces in the engaging segment 201, when repeated many times, can lead to fatigue and failure of the connection to the anchor, for example by the wire breaking. The preferred design avoids this by effectively "shorting" the engaging segment 201 of the wire 200 so that the current passing through the engaging segment 201 of the wire 200 is significantly less than the current passing through the rest of the wire 200 and so a current that induces heating of the rest of the wire sufficient to cause contraction may be employed and limited so that it is not sufficient to cause the engaging segment 201 of the wire 200 to heat to the $A_s$ threshold, thus preventing or substantially reducing any thermally activated forces in the engaging segment 201 of the wire 200.

It should be noted that it is not essential that the electrical resistance of the anchor body 101 be less than the electrical resistance of the wire 200. For example, if the resistance of the anchor body 101 is about equal to the resistance of the wire 200, then the current flowing through the engaging segment 201 of the wire 200 is reduced to about half of the current flowing through the rest of the wire. If the resistance of the anchor body 101 is about two times the resistance of the wire 200, then the current flowing through the engaging segment 201 of the wire 200 is reduced to about two thirds of the current flowing through the rest of the wire, which may still be adequate, by suitable choice of the current level, to prevent Joule heating of the engaging segment 201 of the wire 200 sufficient to cause it to reach the $A_s$ threshold temperature at which it would start to attempt to deform.

In some embodiments, for example where activation of the wire is done by applying heat convectively, the anchor body, by being thermally conductive (and not necessarily electrically conductive), can prevent the thermal activation of the engaging segment 201 of the wire 200 by presenting a combined thermal mass that absorbs enough of the heat applied to the engaging segment 201 of the wire 200 to keep the temperature of the engaging segment 201 of the wire 200 below the $A_s$ threshold while the rest of the wire is heated above the $A_s$ threshold. Such activation is typically performed for short periods which are insufficient for the combined, thermally engaged anchor body 101 and engaging segment 201 of the wire 200 to reach the $A_s$ threshold temperature.

Figure 7:
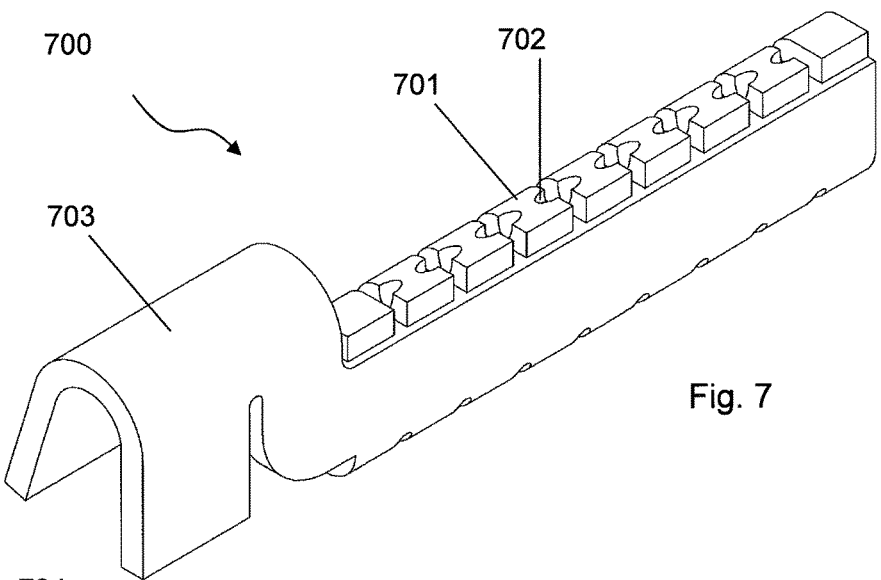
FIG. 7 is a perspective view of an anchoring device for anchoring multiple strands of a thermally responsive ligature using a second embodiment of an anchor.
Figure 8:
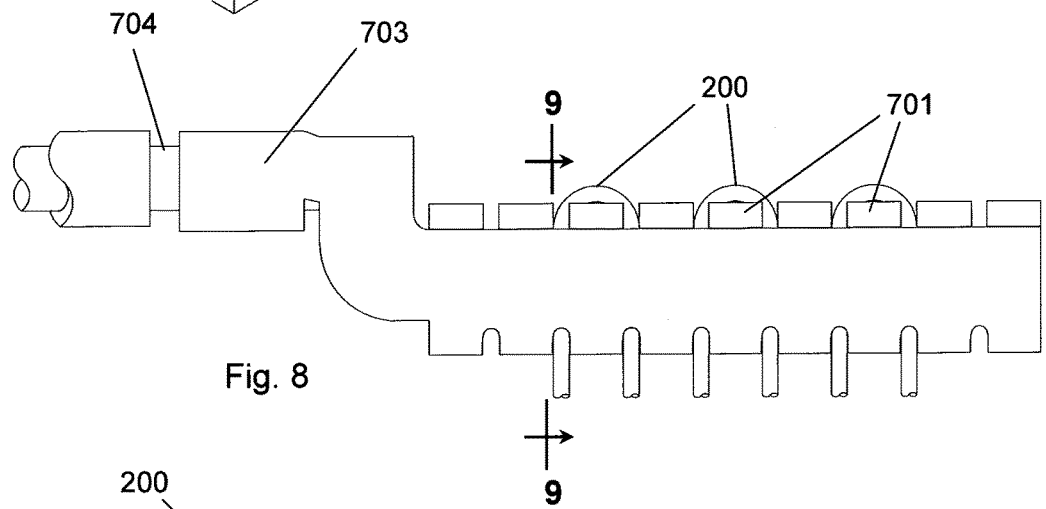
FIG. 8 is a side view of the device of FIG. 7 with three engaging segments of an SMA wire engaged with three of the anchors in the device.
Figure 9:
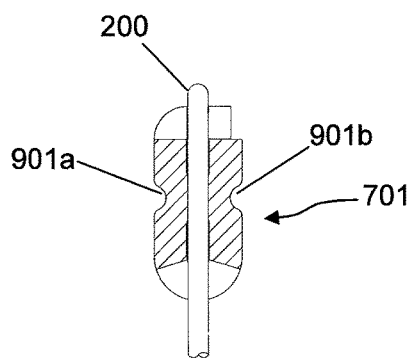
FIG. 9 is a cross sectional view through the lines 9-9 of FIG. 8.

FIGS. 7-9 depict a device 700 that includes multiple anchors, each anchor 701 being a second embodiment of the invention. Each anchor has a generally "U" shaped engaging surface with a flat upper surface. Vertical grooves 702 with a curved upper portion on each side, and a relatively straight vertical lower portion, define the anchor body and its outer engaging surface, which engages the engaging segment of the wire 200 as shown in FIGS. 8 and 9. The width of the grooves 702 is somewhat greater than the diameter of the wire 200 and is used to locate the engaging segment 201 relative to the anchor 701. Once the wire 200 is placed in engagement with the engaging surface of the anchor 701, force can be applied on opposing sides of the anchor towards the wire (e.g. into the page in FIG. 8 on the visible side, and left and right towards the wire 200 in FIG. 9), so that the clamping component of the anchor 701 press against the wire on opposing sides and clamp the wire, maintaining it in engagement with the anchor. Where the forces are applied over a limited vertical portion of the anchor, they may result in indentations 901a, 901b as seen in FIG. 9. The material used to form the anchor is selected so that the two portions of the clamping components can bend towards the wire under such force, and remain in the bent/clamping position after the force is removed. It should be noted that the fact that the second embodiment of an anchor 701 shown in the figures has an upper portion that has a curved outer surface on the left in FIG. 9 and a flat outer surface on the right in FIG. 9 is of no importance to the invention and is simply related to the method by which the device 700 and anchors 701 were formed.

An integral power wire connection 703 is provided such that a power wire 704 can be connected to the device 700. This connection permits the electrical connection necessary to introduce current into, or sink current away from, the engaging segments of the wire 200. The connection 703 in this embodiment is a traditional two-tab wire crimp. Other connection methods, such as soldering or a screw terminal, can alternatively be employed.

FIG. 10 depicts a third embodiment of an anchor 1000. The anchor 1000 is formed from a single piece of metal. The central portion 1001 is the anchor body, and the clamping component consists of the two portions 1003a, 1003b extending from the anchor body 1001. The anchor body 1001 has a smoothly curved engaging surface 1002 for engaging the curved portion 202 of the wire 200, and each of the two portions of the clamping component 1003a, 1003b has a hole or opening 1004 adjacent to the anchor body 1001, and extending through the portion of the clamping component 1003a, 1003b. The opening 1004 is sized and shaped to allow the wire 200 to pass through the opening 1004 (as depicted in FIG. 11a). Each portion of the claiming component 1003a, 1003b also has an indentation 1005 that facilitates the application of force by a hard indentation tool to each portion towards the anchor body 1001. Applying such forces causes a sub-portion of each portion of the clamping component 1003a, 1003b to press against a portion of the wire passing through the hole 1004 in that portion to press the wire against the anchor body 1001 (being a portion of the inner surface of the hole 1004 directly adjacent to the anchor body 1001). The use of a deformable ductile material, such as brass, means that the deformed configuration is maintained and the engaging segment of the wire 200 is maintained in thermal and/or electrical communication with the anchor body 1001. The underside of the anchor 1000 is a flat surface to facilitate attachment to a structural member by way of soldering. When soldered to a pad of a printed circuit board, current may be introduced into, or sinked away from, the anchor 1000. Alternatively the anchor may float on the member and use the wire 200 and the mechanical biasing force to maintain its position relative to the member.

FIGS. 11a and 11b depict an actuator 1100, which is not activated in FIG. 11a and is activated in FIG. 11b. The actuator 1100 has two members 1101a, 1101b that are movable towards each other. The members 1101a, 1101b are connected by an SMA wire 200 that connects to the upper member 1101a via one anchor 1000 and connects to the lower member 1101b via two anchors 1000. The actuator 1100 also has a biasing mechanism, such as a spring or multiple springs, that biases the two members away from each other, exerting a stretching force on the SMA wire 200.

When a current is applied through the wire 200 in FIG. 11a, the wire 200 heats until it passes the $A_s$ threshold temperature, at which point the wire contracts and pulls the two members 1101a, 1101b closer together as shown in FIG. 11b. The shorting of the engaging segment of the wire where it engages the anchors substantially prevents any deformational forces from being applied within those engaging segments of the wire by keeping the temperature of the engaging segments of the wire below the $A_s$ threshold temperature.

After the heating is discontinued, and if the ambient temperature around the wire is less than $M_f$, the biasing force will return the wire to its initial state as the temperature of the wire falls past $M_s$ to $M_f$ or less.

FIG. 12 depicts a more complex actuator 1200 with an upper member 1201 and lower member 1202 connected by SMA wire 200. The wire 200 is connected by 12 W-shaped anchors 100 similar to the anchor depicted in FIGS. 3-6. The connection of the wire 200 to the lower member 1202 is not shown, but is done by a combination of anchors, which may be include multiple embodiments of anchors used together, such as items 100 and 700. The wire 200 may be a single serpentine wire. The wire 200, anchors, and power wires 1203 form an electrical circuit. Driving sufficient current through the electrical circuit will cause the wire 200 to contract and cause the members 1201, 1202 to move towards each other.

It is generally preferred that the engaging segment of the ligature have a (preferably smooth) 180 degree curve (as in FIG. 2a) so that the clamping portions of the engaging segment of the ligature are substantially parallel, for example to facilitate actuator designs such as shown in FIG. 12. However, this is not essential, and the curve may be less the 180 degrees in some designs. However, the curve must be greater than zero degrees, and normally at least 90 degrees, so that the ligature changes direction where it is connected to an anchor so that the deformation of the wire when it is activated causes the curved portion of the wire to exert a downward force (in the orientation shown in FIG. 4 for example) on the engaging surface of the anchor body. The change in direction of the wire in the engaging segment also helps further reduce the chances of the wire being pulled out or slipping.

SMA tape may be used as the ligature rather than SMA wire. Such tape is substantially flat with a width significantly greater than its thickness. The curved portion of the ligature in such embodiments bends along an axis parallel to the width of the tape.

In an actuator, the ligature may be surrounded by gas (e.g. air) or liquid, or be in a vacuum. Suspension in liquid may be used, for example, to reduce recovery time and aid heat dissipation after the heating of the ligature has been discontinued. When suspended in liquid the liquid may be the working fluid of a hydraulic circuit. When suspended in a liquid the anchors may be placed on either side of the fluid boundary. A fluid boundary may be established around the wires by sandwiching a pliable gasket material between two boards. A fluid boundary may be established around the anchors and mounting board by creating a moulded sealing surface using a potting compound, such as epoxy. Objects in contact with the fluid boundary may be electrically isolated from the SMA electrical circuit.

It should be understood that the above-described embodiments of the present invention, particularly, any "preferred" embodiments, are only examples of implementations, merely set forth for a clear understanding of the principles of the invention. Many variations and modifications may be made to the above-described embodiment(s) of the invention as will be evident to those skilled in the art. That is, persons skilled in the art will appreciate and understand that such modifications and variations are, or will be, possible to utilize and carry out the teachings of the invention described herein.

Where, in this document, a list of one or more items is prefaced by the expression "such as" or "including", is followed by the abbreviation "etc.", or is prefaced or followed by the expression "for example", or "e.g.", this is done to expressly convey and emphasize that the list is not exhaustive, irrespective of the length of the list. The absence of such an expression, or another similar expression, is in no way intended to imply that a list is exhaustive. Unless otherwise expressly stated or clearly implied, such lists shall be read to include all comparable or equivalent variations of the listed item(s), and alternatives to the item(s), in the list that a skilled person would understand would be suitable for the purpose that the one or more items are listed.

The words "comprises" and "comprising", when used in this specification and the claims, are used to specify the presence of stated features, elements, integers, steps or components, and do not preclude, nor imply the necessity for, the presence or addition of one or more other features, elements, integers, steps, components or groups thereof.

The scope of the claims that follow is not limited by the embodiments set forth in the description. The claims should be given the broadest purposive construction consistent with the description and figures as a whole.

What is claimed is:

1. An anchor for a thermally responsive ligature that deforms when heated, the ligature being configured to have an engaging segment for engaging the anchor, the engaging segment being a segment of the ligature comprising two clamping portions and a curved portion therebetween, the anchor comprising a body and a configurable clamping component, the anchor body comprising a thermally conductive material or an electrically conductive material and having an engaging surface for engaging the curved portion of the engaging segment of the ligature, the clamping component being configured to allow the clamping portions of the engaging segment of the ligature to pass between the body and the clamping component when the curved portion of the engaging segment is engaging the engaging surface of the anchor body so that portions of the clamping component proximate to the clamping portions of the engaging segment of the ligature can be moved towards the anchor body to reconfigure the clamping component so that the portions of the clamping component press the clamping portions of the engaging segment of the ligature against the anchor body and maintain the engaging segment of the ligature in thermal or electrical communication with the anchor body.

2. The anchor of claim 1, wherein the anchor body is attachable to a first member of a device having a second member connected to the first member by the thermally responsive ligature, so that when the anchor body is attached to the first member of the device, the engaging segment of the ligature is in thermal or electrical communication with the anchor body, with the curved portion of the engaging segment of the ligature engaging the engaging surface of the anchor body, and the clamping portions of the ligature pressed against the anchor body by the clamping component after the clamping component has been reconfigured to maintain the engaging segment of the ligature in thermal or electrical communication with the anchor body,
wherein when the ligature is heated, the ligature deforms and applies force to the anchor body towards the second member, causing the members to move towards each other,
and wherein when the ligature is heated, the temperature increase in the engaging segment of the ligature is sufficiently limited by heat transfer to the anchor body or by reduction of current passing through the engaging segment of the ligature because of current passing through the anchor body that deformation of the engaging segment of the ligature is prevented or substantially reduced relative to segments of the ligature not in contact with the anchor.

3. The anchor of claim 1, wherein the curved portion of the engaging segment of the ligature comprises two curved sub-portions and a flattened sub-portion therebetween, and the engaging surface of the anchor body comprises a flat portion for engaging a portion of the flattened sub-portion of the engaging segment of the ligature.

4. The anchor of claim 1, wherein the engaging surface of the anchor body and the curved portion of the engaging segment are continuously curved so that when the clamping portions of the engaging segment of the ligature are clamped against the anchor body, the ligature engages the curved surface of the anchor body along the full length of the engaging segment of the ligature.

5. The anchor of claim 1, wherein the ligature is electrically conductive and a portion of the anchor body comprising a portion of the engaging surface of the anchor body is electrically conductive so that when the engaging segment of the ligature is engaged with the anchor body, the electrically conductive portion of the anchor body electrically connects the clamping portions of the engaging segment of the ligature.

6. The anchor of claim 5, wherein the electrically conductive portion of the anchor body presents an electrical resistance less that the electrical resistance of the engaging segment of the ligature, so that when a current, I, flows through segments of the ligature not in contact with the anchor, the amount of current flowing through the engaging segment of the ligature is less than one half of I.

7. The anchor of claim 5, wherein the anchor body is attachable to a first member of a device having a second member attached to the first member by the ligature, so that when the anchor body is attached to the first member of the device, the engaging segment of the ligature is electrically engaged with the anchor body, with the curved portion of the engaging segment of the ligature engaging the engaging surface of the anchor body, and the clamping portions of the ligature pressed against the anchor body by the clamping component after it has been reconfigured to maintain the engaging segment of the ligature in electrical communication with the anchor body,
wherein when sufficient current passes through the ligature to cause the ligature to heat sufficiently to cause some portions of the ligature to deform, the ligature applies force to the anchor body towards the second member, causing the members to move towards each other,
and wherein deformation of the engaging segment of the ligature is substantially prevented by the fraction of the current flowing through the engaging segment of the ligature being limited as a result of the current flowing through the anchor body.

8. The anchor of claim 5, wherein the anchor body is metal.

9. The anchor of claim 5, wherein the anchor further comprises a feature for electrically connecting the electrically conductive portion of the anchor body to a power source.

10. The anchor of claim 9, wherein the feature for electrically connecting the electrically conductive portion of the anchor body to a power source is a solder pad and the power source is connectable to the feature through a mating solder pad on a printed circuit board.

11. The anchor of claim 1, wherein the ligature is a shape memory alloy wire.

12. The anchor of claim 1, wherein the ligature is a shape memory alloy tape.

13. The anchor of claim 1, wherein the anchor body and clamping component are integrally formed from a single piece of metal.

14. The anchor of claim 13, wherein the anchor body comprises a U-shaped portion of the piece of metal, and the clamping component comprises two arms, each arm being bendably connected to one end of the anchor body and extending along a portion of a side of the anchor body proximate to and spaced apart from the anchor body, and wherein the anchor comprises two openings sized and shaped to accommodate the ligature, each opening being proximate to the anchor body and to one of the arms.

15. The anchor of claim 1, wherein the clamping component is a metal ring having an inner diameter greater than the sum of (a) two times the thickness of the ligature and (b) the thickness of the portion of the anchor body proximate to the clamping portions of the engaging segment of the ligature.

16. The anchor of claim 1, wherein the anchor includes locating features configured to receive the engaging segment of the ligature.

17. The anchor of claim 16, wherein the locating features comprise two grooves as locating features, each groove being configured to receive one of the clamping portions of the engaging segment of the ligature.

18. An actuator comprising first and second members, a thermally responsive ligature connected to the second member, and the anchor of claim 1 attached to the first member, the engaging segment of the ligature being in thermal or electrical communication with the anchor body, with the curved portion of the engaging segment of the ligature engaging the engaging surface of the anchor body, and the clamping portions of the ligature pressed against the anchor body by the clamping component after the clamping component has been reconfigured to maintain the engaging segment of the ligature in thermal or electrical communication with the anchor body, wherein when the ligature is heated sufficiently, the ligature deforms and applies force to the engaging surface of the anchor body towards the second member, causing the members to move towards each other.

19. The actuator of claim 18, wherein the actuator further comprises a biasing mechanism configured to move the first and second members back to their starting positions after the heating has been discontinued.

20. An anchoring device comprising a plurality of anchors, each anchor being an anchor as claimed in claim 1, the anchoring device being configured so that for each of the anchors, the engaging surface of the anchor is engageable with an engaging segment of a thermally responsive ligature so that the clamping portions of the ligature are pressed against the anchor body by the clamping component of the anchor after the clamping component has been reconfigured to maintain the engaging segment of the ligature in thermal or electrical communication with the anchor body.

* * * * *